(12) United States Patent
Ray et al.

(10) Patent No.: US 11,589,848 B2
(45) Date of Patent: Feb. 28, 2023

(54) HARVESTING CANCELLOUS BONE AND MARROW FROM POSTERIOR SUPERIOR ILIAC SPINE USING BONE PRESS

(71) Applicant: H & M INNOVATIONS, LLC, Wilmington, NC (US)

(72) Inventors: Joel W. Ray, Cape Girardeau, MO (US); Robert Sean Hensler, Wilmington, NC (US)

(73) Assignee: H & M INNOVATIONS, LLC, Wilmington, NC (US)

( * ) Notice: Subject to any disclaimer, the term of this patent is extended or adjusted under 35 U.S.C. 154(b) by 234 days.

(21) Appl. No.: 16/916,012

(22) Filed: Jun. 29, 2020

(65) Prior Publication Data

US 2020/0367865 A1    Nov. 26, 2020

Related U.S. Application Data

(60) Provisional application No. 62/868,779, filed on Jun. 28, 2019.

(51) Int. Cl.
*A61B 10/02* (2006.01)

(52) U.S. Cl.
CPC .... *A61B 10/025* (2013.01); *A61B 2010/0258* (2013.01)

(58) Field of Classification Search
CPC ................ A61B 10/025; A61B 2010/0258
See application file for complete search history.

(56) References Cited

U.S. PATENT DOCUMENTS

| | | | | |
|---|---|---|---|---|
| 4,430,084 A | * | 2/1984 | Deaton | A61M 1/00 206/520 |
| 2002/0177785 A1 | * | 11/2002 | Brannon | A61B 5/150755 600/562 |
| 2004/0191897 A1 | * | 9/2004 | Muschler | A61B 17/32002 435/325 |
| 2007/0225665 A1 | * | 9/2007 | Perez-Cruet | A61M 1/79 604/317 |
| 2008/0221580 A1 | * | 9/2008 | Miller | F41A 17/46 606/80 |
| 2012/0279933 A1 | * | 11/2012 | Hensler | A61M 1/79 210/232 |
| 2012/0330220 A1 | * | 12/2012 | Hensler | A61M 1/0001 604/319 |

* cited by examiner

*Primary Examiner* — Christian A Sevilla
(74) *Attorney, Agent, or Firm* — Tillman Wright, PLLC; Chad D Tillman

(57) ABSTRACT

A method of harvesting cancellous bone and marrow from an individual's posterior superior iliac spine using a bone press apparatus includes: creating an opening in cortical bone of the posterior superior iliac spine; accessing through the opening and loosening for extraction cancellous bone and bone marrow; inserting a suction apparatus through the opening and extracting the loosened cancellous bone and bone marrow, the suction apparatus being attached to a first lid of a collection container, the first lid of the collection container having a suction port to which a suction source is connected; disconnecting the suction source from the suction port and replacing the first lid with a second lid having a suction port and a plunger with a press head; filtering the extracted liquid by depressing the plunger; and pouring the filtered liquid through the suction port of the second lid into another cup.

6 Claims, 2 Drawing Sheets

HARVESTING CANCELLOUS BONE AND MARROW FROM POSTERIOR SUPERIOR ILIAC SPINE USING BONE PRESS

CROSS-REFERENCE TO RELATED APPLICATION

The present application is a U.S. nonprovisional patent application of, and claims priority under 35 U.S.C. § 119(e) to, U.S. provisional patent application 62/868,779, filed Jun. 28, 2019, which '779 application is incorporated by reference herein. The disclosure of the '779 application is set forth in the appendix, which is incorporated by reference herein.

COPYRIGHT STATEMENT

Any new and original work of authorship in this document—including any source code—is subject to copyright protection under the copyright laws of the United States and other countries. Reproduction by anyone of this document as it appears in official governmental records is permitted, but otherwise all other copyright rights whatsoever are reserved.

BACKGROUND OF THE INVENTION

The invention generally relates to procedures and devices used therein for shallow-core harvesting of cancellous bone and marrow from the posterior superior iliac spine ("PSIS") and, preferably, shallow-core harvesting of autologous cancellous bone and marrow from the posterior superior iliac spine immediately prior to an anterior cervical discectomy/fusion ("ACDF"), wherein the harvested cancellous bone and marrow is used in that individual during the ACDF procedure. The procedure of the invention has been nicknamed the "Ray Iliac Procedure" and is set forth in detail in the following pages and in the incorporated appendix. The Ray Iliac Procedure is intended for use in the orthopedic surgical field.

The Ray Iliac Procedure is based on a repurposed use of a bone press apparatus as disclosed, for example, in U.S. Pat. No. 8,920,393, which is incorporated herein by reference. Such bone press apparatus are commercially sold by Hensler Surgical Products, LLC, of Wilmington, N.C. The bone press apparatus was designed for harvesting high-speed drilled bone during spinal procedures, which harvested bone was found to be a moldable and malleable matrix that could be reused in the patient to increase fusion healing rates.

Prior techniques include deep coring and large openings cut in the crest, resulting in potential for increased bleeding and very frequently postoperative remote site pain. The Ray Iliac Procedure avoids deep-coring and large cutouts of the crest, thereby avoiding such potential disadvantages of the prior techniques.

SUMMARY OF THE INVENTION

As used herein, the Ray Iliac Procedure is a method of harvesting cancellous bone and marrow from an individual's posterior superior iliac spine using a bone press apparatus. The method comprises the steps of: creating an opening in cortical bone of the posterior superior iliac spine; accessing through the opening and loosening for extraction cancellous bone and bone marrow; inserting a suction apparatus through the opening and extracting the loosened cancellous bone and bone marrow, the bone marrow comprising a liquid, the suction apparatus being attached to a first lid of a collection container, the first lid of the collection container having a suction port to which a suction source is connected; after extracting the cancellous bone and bone marrow, disconnecting the suction source from the suction port of the first lid; removing the first lid of the collection container from the first cup of the collection container; attaching a second lid to the first cup of the collection container, the second lid having a suction port and a plunger with a press head configured to filter the extracted liquid contained in the first cup; filtering the extracted liquid by depressing the plunger of the second lid toward a bottom of the first cup; and pouring the filtered liquid from the first cup through the suction port of the second lid into a second cup while depressing the plunger, thereby separating the liquid from a spongy semi-solid mass of cancellous bone that remains in the first cup. The filtered liquid and/or the spongy semi-solid mass of cancellous bone then is preferably used in an anterior cervical discectomy/fusion procedure that is performed on the same individual.

DETAILED DESCRIPTION

Figure 1:
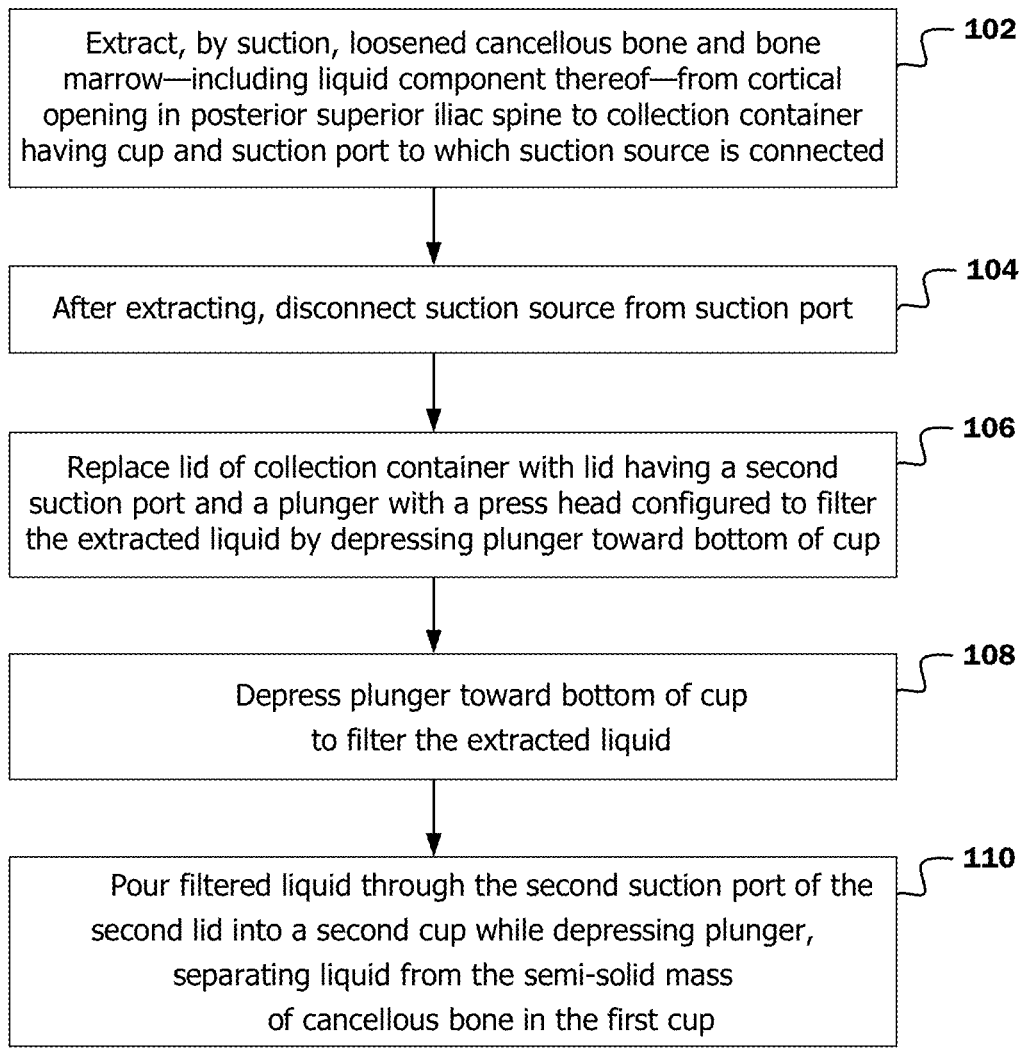
FIG. 1 is a flow chart of steps of the Ray Iliac Procedure for harvesting cancellous bone and bone marrow from the posterior superior iliac spine.

The Ray Iliac Procedure is a method 100 that includes basic steps 102 through 110, a flow chart for which is illustrated in FIG. 1. Step 102 comprises extracting loosened cancellous bone and bone marrow—including a liquid component thereof—by suction to a collection container having a cup and a lid with a suction port to which a suction source is connected. Step 104 comprises, after step 102, disconnecting the suction source from the suction port of the lid. Step 106 comprises replacing the lid with another lid having a suction port and a plunger with a press head that is configured to filter the extracted liquid by depressing the plunger toward a bottom of the cup. Step 108 comprises depressing the plunger toward the bottom of the cup to filter the extracted liquid. Step 110 comprises pouring the filtered liquid from the first cup through the suction port in the second lid into a second cup while depressing the plunger, thereby separating the liquid from a semi-solid mass of cancellous bone that remains in the first cup.

The Ray Iliac Procedure takes generally less than 5 minutes if done without complications and if more bone for grafting is not required beyond the initial yields.

The Ray Iliac Procedure additionally includes the following details.

Figure 2:
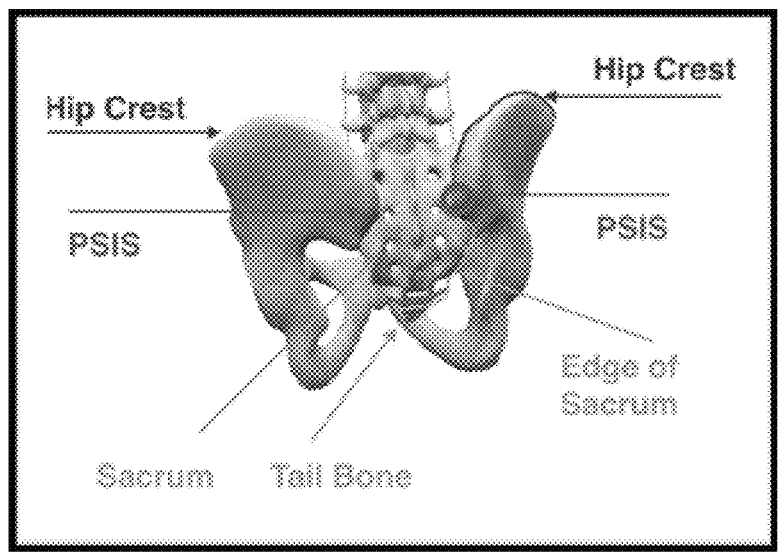
FIG. 2 is an illustration showing the location of the posterior superior iliac spine.

Following the induction of anesthesia, the patient is positioned, prepared, and draped in conventional sterile fashion for the ACDF procedure. Preferably, the right iliac crest is harvested, as noted in FIG. 2.

The specific positioning of the patient uses a bump placed beneath the right hip and taping of the Pannus of the abdomen to maximize exposure to the right anterior superior iliac spine. The bump is placed behind the neck for mild, preoperative tolerated, extension. The positioning of the instrument table is such that the minor procedure for the iliac crest can access related instruments. This simultaneously allows the surgery to be easily shifted to the neck for the anterior cervical approach. The anatomy and incision are drawn out on the skin for the pulling of the pannus in a rostramedial direction so that the incision uses the most superficial access.

The microscope is brought in behind the surgeon's right shoulder so when shifting to the cervical exposure, the surgeon has the scope in position behind the left shoulder. The positioning of the assistant is on the right side facilitating visual access using the microscope for collaborative exposure dissection as well as rapid closure.

A local anesthetic is administered comprising 5 cc of ½% lidocaine with 1 to 200,000 epinephrine by injection under the skin at the chosen harvest site.

A sharp incision is made along the right anterior iliac crest starting at 1 cm posterior to the right anterior superior iliac crest spine. The skin further is pulled rostrally as this is being done so the healing incision lies just inferior to the crest. This places the harvest site within the maximal thickness of the crest itself. Furthermore, the incision is placed in this manner so that once the tape's tension is released, the area relaxes and the incision sits immediately inferior to the crest and thus has the best healing opportunity.

Figure 3:
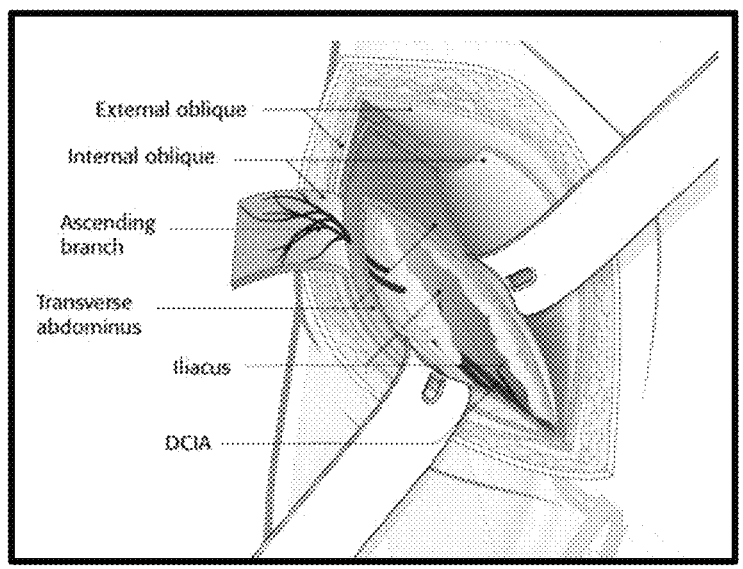
FIG. 3 is an illustration showing the location of the posterior superior iliac spine.

A 1½ cm stab incision is taken down through the periosteum in the midline of the superior crest with a 10 blade. The assistant uses either a very thin anterior cervical Cloward retractor and or a wide nerve root retractor. FIG. 3 illustrates use of retractors. This brings the incision down to the midline of the anterior superior crest using a sucker and a bovie. The surgeon and assistant collaboratively progress the dissection using the retractors and mutual microscope visualization by the surgeon and assistant.

An 11 or 12 French sucker tip is secured onto the distal end of tubing that terminates at the other end at an 80 cc collection container of the bone press apparatus. A Midas Rex or equivalent drill with an AM8 bit (or an equivalent cutting bur) is used to make a 2 to 3 mm hole in the crest just beyond the cortical bone tables. The drill, as well as small curettes, are used to sharply insert into the created hole to remove and loosen cancellous bone and excite the bone marrow. The French sucker tip then is inserted through the hole to suction both bone liquid marrow and spicules of bone.

Efforts should be made not to break through the deeper cortices of the iliac crest.

The amount of bone and marrow harvested in the 80 cc collection container should be monitored and the suctioning halted when a sufficient amount has been obtained as specified by the surgeon.

While efforts are made to remain subperiosteal, suction can be applied in the medially, laterally, rostral, and caudal directions to harvest essentially as much liquid bone marrow and cancellous bone chips as are required.

During suctioning the microscope can be used by the surgeon and the assistant to observe the progress of the suctioning of the bone.

Once the required amount of bone has been collected, suctioning is halted and the lid of the collection container is unscrewed from the cup of the collection container and handed to a scrub tech. If more harvesting is needed, the foregoing steps are then repeated by screwing the lid onto another cup and restarting suction.

Upon completion of harvesting, 1 or 2 pieces of Gel Foam are placed into the drilled hole, which typically resolves any residual bleeding which typically is minimal. Bone wax also may be used if needed.

The retractors are then removed and a small temporary island dressing is placed.

Closure can be completed at the end of the case with inverted 3-0 Vicryl sutures and island dressing.

The surgical team and equipment then is rapidly and easily repositioned to initiate and complete the ACDF procedure.

The cup received by the scrub tech is processed to separate the liquid bone marrow from the cancellous bone. This is accomplished by screwing the second lid of the bone press apparatus having the plunger onto the cup and depressing the plunger. Depressing the plunger filters the liquid in the cup, compressing the cancellous bone against the bottom of the cup. During these steps, no suction is used and no suction line is attached to the suction port on the side of the second lid is left. Instead, the suction port is used to pour out the liquid marrow in the cup by titling the cup while continuing to depress the plunger. This pressing and tilting should be repeated to ensure maximum separation of the liquid bone marrow from the cancellous bone. Once the liquid marrow has been poured out, the second lid is unscrewed from the cup and the cancellous bone—in the form of a spongy mass at the bottom of the cup—is withdrawn from the cup using a periosteal, curette, Penfield or similar instrument and is staged onto an absorbable pad for use in the patient during the ACDF procedure.

As will be appreciated, the Ray Iliac Procedure can be quickly efficiently performed prior to the ACDF procedure.

Additional details as well as observations and benefits of the Ray Iliac Procedure are disclosed in the appendix, which is incorporated herein by reference.

What is claimed is:

1. A method of harvesting cancellous bone and marrow from an individual's posterior superior iliac spine using a bone press apparatus, comprising the steps of:
   (a) creating an opening in cortical bone of the posterior superior iliac spine;
   (b) accessing through the opening and loosening for extraction cancellous bone and bone marrow;
   (c) inserting a suction apparatus through the opening and extracting the loosened cancellous bone and bone marrow, the bone marrow comprising a liquid, the suction apparatus being attached to a first lid of a collection container, the first lid of the collection container covering a first cup of the collection container and having a suction port to which a suction source is connected;
   (d) after extracting the cancellous bone and bone marrow, disconnecting the suction source from the suction port of the first lid;
   (e) removing the first lid of the collection container from the first cup of the collection container;
   (f) attaching a second lid to the first cup of the collection container, the second lid having a suction port and a plunger with a press head configured to filter the extracted liquid contained in the first cup;
   (g) filtering the extracted liquid by depressing the plunger of the second lid toward a bottom of the first cup; and
   (h) pouring the filtered liquid from the first cup through the suction port of the second lid into a second cup while depressing the plunger, thereby separating the liquid from a spongy semi-solid mass of cancellous bone that remains in the first cup.

2. The method of claim 1, further comprising using the filtered liquid and the spongy semi-solid mass of cancellous bone in an anterior cervical discectomy/fusion procedure that is performed on the individual.

3. The method of claim 1, further comprising the step of using at least one of the filtered liquid and the spongy semi-solid mass of cancellous bone in an anterior cervical discectomy/fusion procedure that is performed on the individual.

4. A method of harvesting cancellous bone and marrow from an individual, comprising the steps of:
   (a) creating an opening in cortical bone of an iliac spine;
   (b) accessing through the opening and loosening for extraction cancellous bone and bone marrow;
   (c) inserting a suction apparatus through the opening and extracting the loosened cancellous bone and bone marrow, the bone marrow comprising a liquid, the suction apparatus being attached to a first lid of a collection container, the first lid of the collection container having a suction port to which a suction source is connected;
   (d) after extracting the cancellous bone and bone marrow, disconnecting the suction source from the suction port of the first lid;
   (e) replacing the first lid of the collection container with a second lid, the second lid having a suction port and a plunger with a press head configured to filter the extracted liquid contained in the collection container;
   (f) filtering the extracted liquid by depressing the plunger of the second lid; and
   (g) pouring the filtered liquid from the collection container through the suction port of the second lid into a cup while depressing the plunger, thereby separating the liquid from a spongy semi-solid mass of cancellous bone that remains in the collection container.

5. The method of claim 4, further comprising using the filtered liquid and the spongy semi-solid mass of cancellous bone in an anterior cervical discectomy/fusion procedure that is performed on the individual.

6. The method of claim 4, further comprising the step of using at least one of the filtered liquid and the spongy semi-solid mass of cancellous bone in an anterior cervical discectomy/fusion procedure that is performed on the individual.

* * * * *